United States Patent

Varma

[11] 4,435,326
[45] * Mar. 6, 1984

[54] INTERMEDIATES USEFUL IN THE PREPARATION OF 17,17-BIS(SUBSTITUTED THIO)ANDROSTENES

[75] Inventor: Ravi K. Varma, Belle Mead, N.J.

[73] Assignee: E. R. Squibb & Sons, Inc., Princeton, N.J.

[*] Notice: The portion of the term of this patent subsequent to Nov. 30, 1999 has been disclaimed.

[21] Appl. No.: 416,181

[22] Filed: Sep. 9, 1982

[51] Int. Cl.³ .............................................. C07J 1/00
[52] U.S. Cl. .............................. 260/397.3; 260/397.45
[58] Field of Search ......................... 260/397.3, 397.45

[56] References Cited

U.S. PATENT DOCUMENTS 4,361,559  11/1982  Varma ........................... 260/397.45

Primary Examiner—Elbert L. Roberts
Attorney, Agent, or Firm—Lawrence S. Levinson; Donald J. Barrack

[57] ABSTRACT

Androstenes having the formula

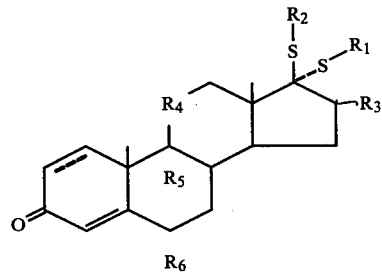

wherein
$R_1$ hydrogen and $R_2$ is alkyl, cycloalkyl, aryl, arylalkyl, alkylthioalkyl, alkoxyalkyl, alkanoyloxyalkyl, aroyloxyalkyl, alkoxycarobnylalkyl, carboxyalkyl, or arylalkyl, or $R_1$ is alkanoyl or aroyl and $R_2$ is alkyl;
$R_3$ is hydrogen, hydroxy, alkoxy, aryloxy, oxo, methylene, alkylthio, arylthio, alkanoyl, alkanoyloxy, or halogen;
$R_4$ is carbonyl, $\beta$-hydroxymethylene or $\beta$-acetyloxymethylene;
$R_5$ is hydrogen or halogen; and $R_6$ is hydrogen, methyl, hydroxy, alkanoyl or halogen are useful intermediates for the preparation of steroids having antiinflammatory activity.

6 Claims, No Drawings

INTERMEDIATES USEFUL IN THE PREPARATION OF 17,17-BIS(SUBSTITUTED THIO)ANDROSTENES

RELATED APPLICATIONS

U.S. patent application Ser. No. 294,680, filed Aug. 20, 1981, now U.S. Pat. No. 4,361,559, issued Nov. 30, 1982, discloses 3-ketonadrostenes having in the 17-position the substituents $R_a$—S— and $R_b$—S— wherein $R_a$ and $R_b$ are the same or different and each is alkyl, cycloalkyl or aryl. The compounds are antiinflammatory agents.

U.S. patent application Ser. No. 396,178, filed July 7, 1982, discloses 3-ketoandrostenes having in the 17-position the substituents $R_c$—S— and $R_d$—S— wherein one of $R_c$ and $R_d$ is alkyl, cycloalkyl, aryl, arylalkyl, or —CH$_2$X wherein X is alkylthio, alkoxy, aroyloxy, alkanoyloxy or alkoxycarbonyl, and the other is alkylthioalkyl, alkoxyalkyl, alkanoyloxyalkyl, aroyloxyalkyl, alkoxycarbonylalkyl, carboxyalkyl or arylalkyl. The compounds are antiinflammatory agents.

BRIEF DESCRIPTION OF THE INVENTION

Androstenes having the formula

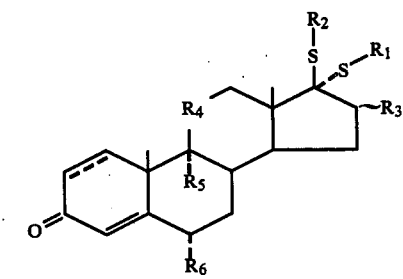

are useful intermediates for the preparation of androstenes having antiinflammatory activity. In formula I, and throughout the specification, the symbols are as defined below.

$R_1$ is hydrogen and $R_2$ is alkyl, cycloalkyl, aryl, arylalkyl, alkylthioalkyl, alkoxyalkyl, alkanoyloxyalkyl, aroyloxyalkyl, alkoxycarbonylalkyl, carboxyalkyl, or arylalkyl, or $R_1$ is alkanoyl or aroyl and $R_2$ is alkyl;

$R_3$ is hydrogen, hydroxy, alkoxy, aryloxy, oxo, methylene, alkylthio, arylthio, alkanoyl, alkanoyloxy, or halogen;

$R_4$ is carbonyl, β-hydroxymethylene or β-acetyloxymethylene;

$R_5$ is hydrogen or halogen; and $R_6$ is hydrogen, methyl, hydroxy, alkanoyl or halogen. In formula I, and throughout the specification, a broken line in the steroid rings indicates the optional presence of ethylenic unsaturation.

The term "aryl", as used throughout the specification either individually or as part of a larger group, refers to phenyl or phenyl substituted with one or two alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The term "cycloalkyl", as used throughout the specification, either individually or as part of a larger group, refers to groups having 3,4,5,6 or 7 carbon atoms.

The term "alkanoyl", as used throughout the specification either individually or as part of a larger group, refers to groups having 2 to 13 carbon atoms.

The term "aroyloxy" as used throughout the specification either individually or as part of a larger group, refers to groups having the formula

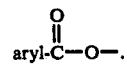

DETAILED DESCRIPTION OF THE INVENTION

The steroids of formula I can be prepared utilizing as starting materials androstenes having the formula

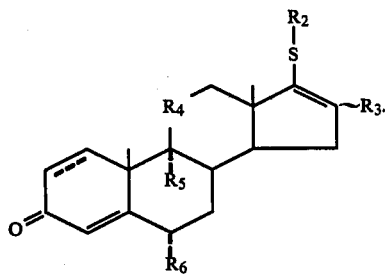

Androstenes of formula II have been described in U.S. patent application Ser. No. 396,178, filed July 7, 1982, the disclosure of which is incorporated herein by reference.

As described in the above referred to patent application, an androstene having the formula

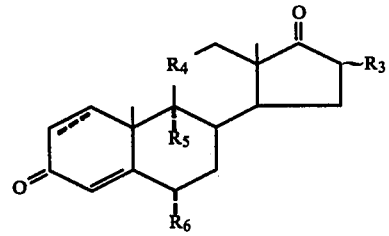

can be reacted with a thiol having the formula

in the presence of a Lewis acid (e.g., boron trifluoride etherate) to yield a steroid having the formula

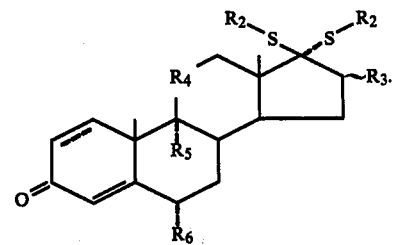

The reaction can be run in an organic solvent (e.g., a halogenated hydrocarbon), or a mixture of organic solvents. The use of glacial acetic acid as the sole solvent, or in admixture with other solvents, improves yields. Reaction conditions are not critical and the reaction can be conveniently run at room temperature, preferably in an inert atmosphere (e.g., argon or nitrogen). Better yields can be obtained with relatively short reaction times (less than 1 hour). The addition of a dimethylformamide dialkyl acetal (preferably dimethylformamide dimethyl acetal) also improves yields.

Conversion of an androstene of formula V to the corresponding starting androstene of formula II can be accomplished by simply heating the steroid, either neat or in an inert solvent (e.g., diethylbenzene or dichlorobenzene). Alternatively, steroids of formula V can be oxidized with a peracid (e.g., m-chloroperbenzoicacid) at low temperature (from about −78° C. to 0° C.) and the resulting monosulfoxide heated in an inert solvent to give an androstene of formula II.

Alternatively, compounds of formula II, wherein $R_3$ is chlorine, bromine, alkylthio, or arylthio can be prepared from the corresponding steroid of formula II wherein $R_3$ is hydrogen. Utilizing the procedure described in U.S. Pat. No. 4,265,815, issued May 5, 1981, a steroid of formula II wherein $R_3$ is chlorine or bromine can be obtained by reacting the corresponding 16-unsubstituted steroid with the appropriate N-halosuccinimide, or with chlorine or bromine, preferably in a halogenated hydrocarbon solvent. Steroids of formula II wherein $R_3$ is alkylthio or arylthio can be obtained by reacting the corresponding 16-unsubstituted steroid with an alkyl or aryl sulfenyl halide, preferably in a halogenated hydrocarbon solvent.

To obtain the steroids of formula I wherein $R_1$ is hydrogen, an androstene of formula II is reacted with hydrogen sulfide. The reaction is run in the presence of a Lewis acid (e.g., boron trifluoride etherate) and will preferably be run at a reduced temperature (i.e., about 0° C. to −20° C.). Particularly when the reaction is run at the reduced temperature, it is stereospecific, and yields the desired steroid of formula I.

To obtain the steroids of formula I wherein $R_1$ is alkanoyl or aroyl and $R_2$ is alkyl, an androstene of formula II wherein $R_2$ is alkyl, is reacted with the appropriate thiol acid having the formula

$R_1'$—SH,  VI wherein $R_1'$ is alkanoyl or aroyl, in the presence of a Lewis acid, using the procedure described above for reacting a compound of formula II with hydrogen sulfide, preferably at −20° C. to −100° C.

The steroids of formula I are useful intermediates for the preparation of androstenes having the formula

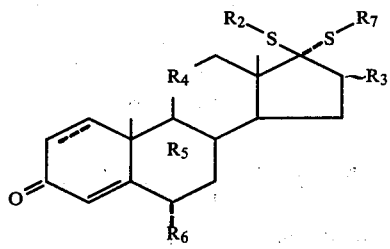

wherein $R_7$ is alkyl or —$CH_2X$ and X is alkylthio, alkoxy, aroyloxy, alkanoyloxy or alkoxycarbonyl. As disclosed in U.S. patent applications Ser. Nos. 294,680, filed Aug. 20, 1981, now U.S. Pat. No. 4,361,559, issued Nov. 30, 1982, and 396,178 filed July 7, 1982, the steroids of formula VII are topical antiinflammatory agents that can be used to treat skin conditions such as dermatitis, psoriasis, sunburn, eczema, neurodermatitis, or anogenital pruritus. The disclosures of these applications are incorporated herein by reference.

A steroid of formula I, wherein $R_1$ is alkanoyl or aroyl, and $R_2$ is alkyl can be treated with base in the presence of an alcohol (e.g., methanol or ethanol) to yield the corresponding steroid of formula I wherein $R_1$ is hydrogen. Exemplary bases are alkali metal cyanides and tertiary amines. A steroid of formula I wherein $R_1$ is hydrogen can be alkylated using conventional techniques to yield the corresponding steroid of formula VII. Exemplary of the alkylation techniques which can be used are the reaction of a steroid of formula I (wherein $R_1$ is hydrogen) with potassium carbonate and an alkyl iodide in the presence of an alcohol (e.g., methanol) and with potassium carbonate and substituted alkyl halides in dimethylformamide.

The following examples are specific embodiments of this invention.

EXAMPLE 1

17β-Ethylthio-9-fluoro-11β-hydroxy-17α-mercaptoandrosta-1,4-diene-3-one

A solution of 2.0 g of 17-ethylthio-9-fluoro-11β-hydroxyandrosta-1,4,16-triene-3-one in dry dichloromethane (120 ml) was cooled and stirred in a bath at about −40° C. and a slow stream of hydrogen sulfide gas was passed into the solution while boron trifluoride etherate (1.2 ml) was added. After about 3.5 to 4.0 hours, the mixture was diluted with chloroform, warmed to room temperature and washed successively with a dilute sodium bicarbonate solution and water. The solution was dried (anhydrous magnesium sulfate), evaporated and the solid residue crystallized from ethyl acetate to afford 1.4 g of the title compound, melting point 239°–242° C.

EXAMPLE 2

11β-Acetyloxy-9-fluoro-17α-mercapto-17β-(methylthio)androsta-1,4-diene-3-one

A solution of 11β-acetyloxy-9-fluoro-17-(methylthio)androsta-1,4,16-triene-3-one (9.0 g) in dry dichloromethane (200 ml) was cooled and stirred in an ice bath and boron trifluoride etherate (6.0 ml) was added. A slow stream of hydrogen sulfide gas was bubbled into the solution for about 3 hours to yield a mixture of the title compound and 11β-acetyloxy-9-fluoro-17-thioandrosta-1,4-diene-3-one. The mixture was poured into water and the product was isolated by extraction with chloroform. The chloroform solution was washed with a saturated sodium bicarbonate solution and water, dried (anhydrous magnesium sulfate) and evaporated to give a mixture of the above compounds as a solid. This was chromatographed on silica gel to isolate the title compound, melting point 182°–186° C. and 11β-acetyloxy-9-fluoro-17-thioandrosta-1,4-diene-3-one, melting point 157°–158° C.

EXAMPLE 3

11β-Acetyloxy-9-fluoro-17α-mercapto-17β-(methylthio)androsta-1,4-diene-3-one

The reaction of 11β-acetyloxy-9-fluoro-17-(methylthio)androsta-1,4,16-triene-3-one (9.0 g) with hydrogen sulfide in the presence of boron trifluoride etherate at 0° C. for 3 hours utilizing the methodology of example 1 yielded (crystallization from ethyl acetate/hexane) 5.2 g of the title compound, melting point 182°–186° C., dec. Chromatography of the mother liquor yielded an additional 1.5 g of the title compound, 11β-acetyloxy-9-fluoro-17-thioandrosta-1,4-diene-3-one, melting point 157°–158° C., and an unidentified minor product.

EXAMPLE 4

17α-Acetylthio-17β-ethylthio-9-fluoro-11β-hydroxyandrosta-1,4-diene-3-one

A suspension of 17-ethylthio-9-fluoro-11β-hydroxyandrosta-1,4,16-triene-3-one (200 mg) in dichloromethane (8.0 ml) containing thiol acetic acid (0.12 ml) was cooled and stirred in a bath at −40° to −45° C. and boron trifluoride etherate (0.1 ml) was added. After 2.5 hours the mixture was poured into a dilute sodium bicarbonate solution under vigorous stirring. The product was then isolated by extraction with chloroform, washed with water, dried (anhydrous magnesium sulfate) and evaporated in vacuo at room temperature to afford the title compound (202 mg), with a consistent H′—NMR spectrum. [On standing at room temperature for a few hours the product reverted back into the starting material by the elimination of thiol acetic acid].

EXAMPLE 5

17-α-Benzoylthio-17β-ethylthio-9-fluoro-11β-hydroxyandrosta-1,4-diene-3-one

By using 9-fluoro-11β-hydroxy-17-(methylthio)androsta-1,4,16-triene-3-one and thiol benzoic acid as starting materials and by following the procedure of example 4, the title compound was prepared and showed a consistent H′—NMR spectrum. [On standing at room temperature for a few hours, it reverted back into the starting steroid by elimination of thiol benzoic acid.]

The following preparations exemplify the utility of the compounds of this invention as intermediates.

PREPARATION 1

9-Fluoro-11β-hydroxy-17β-ethylthio-17α-mercaptoandrosta-1,4-diene-3-one

A solution of 17α-acetylthio-17β-ethylthio-9-fluoro-11β-hydroxyandrosta-1,4-diene-3-one (500 mg; see example 4) in a mixture of dichloromethane (10 ml) and methanol (10 ml) containing sodium cyanide (20 mg) is stirred at room temperature for several hours. The mixture is then diluted with water, the product is isolated by extraction with chloroform, the chloroform solution is evaporated and the residue is crystallized from ethyl acetate to afford the title compound.

PREPARATION 2

17β-Ethylthio-9-fluoro-11β-hydroxy-17α-(methylthio)androsta-1,4-diene-3-one

A solution of 17β-ethylthio-9-fluoro-11β-hydroxy-17α-mercaptoandrosta-1,4-diene-3-one (50 mg) in methanol (3.0 ml) and tetrahydrofuran (3.0 ml) was stirred with potassium carbonate (75 mg) and methyl iodide (0.3 ml) for 3.0 hours. The mixture was then diluted with water, extracted with chloroform, washed with water, dried (anhydrous magnesium sulfate) and evaporated to afford a solid. One crystallization of this from ethyl acetate-hexane gave the analytical specimen of the title compound (35 mg), melting point 257°–258° C.

What is claimed is:

1. A steroid having the formula

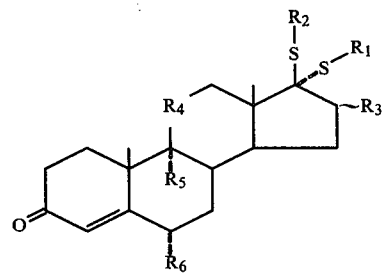

or the 1,2-dehydro derivative thereof wherein $R_1$ is hydrogen;

$R_2$ is alkyl, cycloalkyl, aryl, arylalkyl, alkylthioalkyl, alkoxyalkyl, alkanoyloxyalkyl, aroyloxyalkyl, alkoxycarbonylalkyl, carboxyalkyl, or arylalkyl;

$R_3$ is hydrogen, hydroxy, alkoxy, aryloxy, oxo, methylene, alkylthio, arylthio, alkanoyl, alkanoyloxy, or halogen;

$R_4$ is carbonyl, β-hydroxymethylene or β-acetyloxymethylene;

$R_5$ is hydrogen or halogen; and $R_6$ is hydrogen, methyl, hydroxy, alkanoyl or halogen.

2. A steroid in accordance with claim 1 wherein $R_4$ is β-hydroxymethylene.

3. A steroid in accordance with claim 1 wherein $R_5$ is fluorine.

4. A steroid in accordance with claim 1 wherein $R_6$ is hydrogen.

5. A steroid in accordance with claim 1 wherein $R_4$ is β-hydroxymethylene, $R_5$ is fluorine and $R_6$ is hydrogen.

6. A steroid in accordance with claim 5 wherein $R_1$ is hydrogen and $R_2$ is alkyl.

* * * * *

UNITED STATES PATENT AND TRADEMARK OFFICE
CERTIFICATE OF CORRECTION

PATENT NO. : 4,435,326
DATED : March 6, 1984
INVENTOR(S) : Ravi K. Varma

It is certified that error appears in the above—identified patent and that said Letters Patent is hereby corrected as shown below:

In the Abstract, the structure should read as follows:

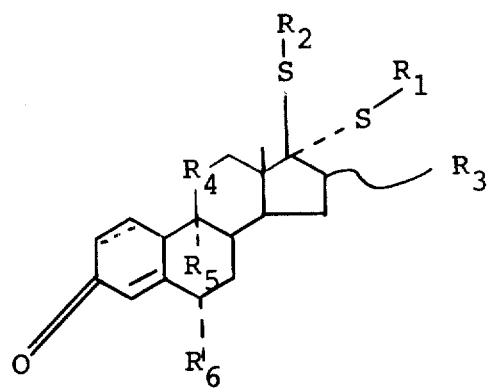

Signed and Sealed this

Twenty-second Day of May 1984

[SEAL]

Attest:

GERALD J. MOSSINGHOFF

Attesting Officer    Commissioner of Patents and Trademarks